United States Patent
Hyun et al.

(10) Patent No.: US 11,408,901 B2
(45) Date of Patent: Aug. 9, 2022

(54) STRIP FOR MEASURING BLOOD LIPIDS

(71) Applicant: GREEN CROSS MEDICAL SCIENCE, Yongin-si (KR)

(72) Inventors: Kyung Hwan Hyun, Seoul (KR); Jung Hyun Lee, Seoul (KR); Gi Wook Kim, Yongin-si (KR)

(73) Assignee: GREEN CROSS MEDICAL SCIENCE, Yongin-si (KR)

( * ) Notice: Subject to any disclaimer, the term of this patent is extended or adjusted under 35 U.S.C. 154(b) by 417 days.

(21) Appl. No.: 16/470,602

(22) PCT Filed: Dec. 15, 2017

(86) PCT No.: PCT/KR2017/014876
§ 371 (c)(1),
(2) Date: Jun. 18, 2019

(87) PCT Pub. No.: WO2018/117549
PCT Pub. Date: Jun. 28, 2018

(65) Prior Publication Data
US 2019/0310270 A1    Oct. 10, 2019

(30) Foreign Application Priority Data
Dec. 21, 2016 (KR) .................. 10-2016-0175318

(51) Int. Cl.
*G01N 33/92* (2006.01)
*G01N 21/78* (2006.01)
(Continued)

(52) U.S. Cl.
CPC ............. *G01N 33/92* (2013.01); *G01N 21/78* (2013.01); *G01N 33/53* (2013.01); *G01N 33/94* (2013.01); *G01N 2405/02* (2013.01)

(58) Field of Classification Search
CPC .... G01N 2405/00; G01N 21/78; G01N 33/94; G01N 33/92; G01N 33/53; G01N 33/525; G01N 33/5306; G01N 2405/02
See application file for complete search history.

(56) References Cited

U.S. PATENT DOCUMENTS 8,158,080 B2   4/2012   Bae et al.
8,221,703 B2   7/2012   Bae et al.
(Continued)

FOREIGN PATENT DOCUMENTS

CN   102460166 A   5/2012
CN   103320499 A   9/2013
(Continued)

OTHER PUBLICATIONS

International Search Report for PCT/KR2017/014876 dated Apr. 9, 2018 (PCT/ISA/210).

*Primary Examiner* — Rebecca M Fritchman
(74) *Attorney, Agent, or Firm* — Sughrue Mion, PLLC

(57) ABSTRACT

The present invention relates to a strip for measuring blood lipids. The strip for measuring blood lipids, of the present invention, presses, with an optimal pressure or to an optimal height, a contact surface of a protruding part of a measurement layer disposed between an upper cover and a lower substrate, so as to improve the uniform diffusion of a biological sample, thereby having an effect of increasing measurement result accuracy of the biological sample.

14 Claims, 6 Drawing Sheets

(51) Int. Cl.
*G01N 33/53* (2006.01)
*G01N 33/94* (2006.01)

(56) References Cited

U.S. PATENT DOCUMENTS

| | | |
|---|---|---|
| 2003/0175153 A1 | 9/2003 | Anaokar et al. |
| 2006/0062688 A1 | 3/2006 | Lawrence |
| 2008/0112848 A1* | 5/2008 | Huffstodt ............... G01N 33/92 422/68.1 |
| 2010/0305419 A1 | 12/2010 | Bae et al. |
| 2010/0311091 A1* | 12/2010 | Bae ....................... G01N 33/92 435/11 |
| 2012/0282634 A1 | 11/2012 | Hughes et al. |

FOREIGN PATENT DOCUMENTS

| | | |
|---|---|---|
| CN | 103391995 A | 11/2013 |
| KR | 10-2010-0130122 A | 12/2010 |
| KR | 10-1058743 B1 | 8/2011 |
| KR | 10-2011-0114748 A | 10/2011 |
| KR | 10-2011-0115216 A | 10/2011 |
| KR | 10-2012-0003340 A | 1/2012 |
| KR | 10-1191329 B1 | 10/2012 |

\* cited by examiner

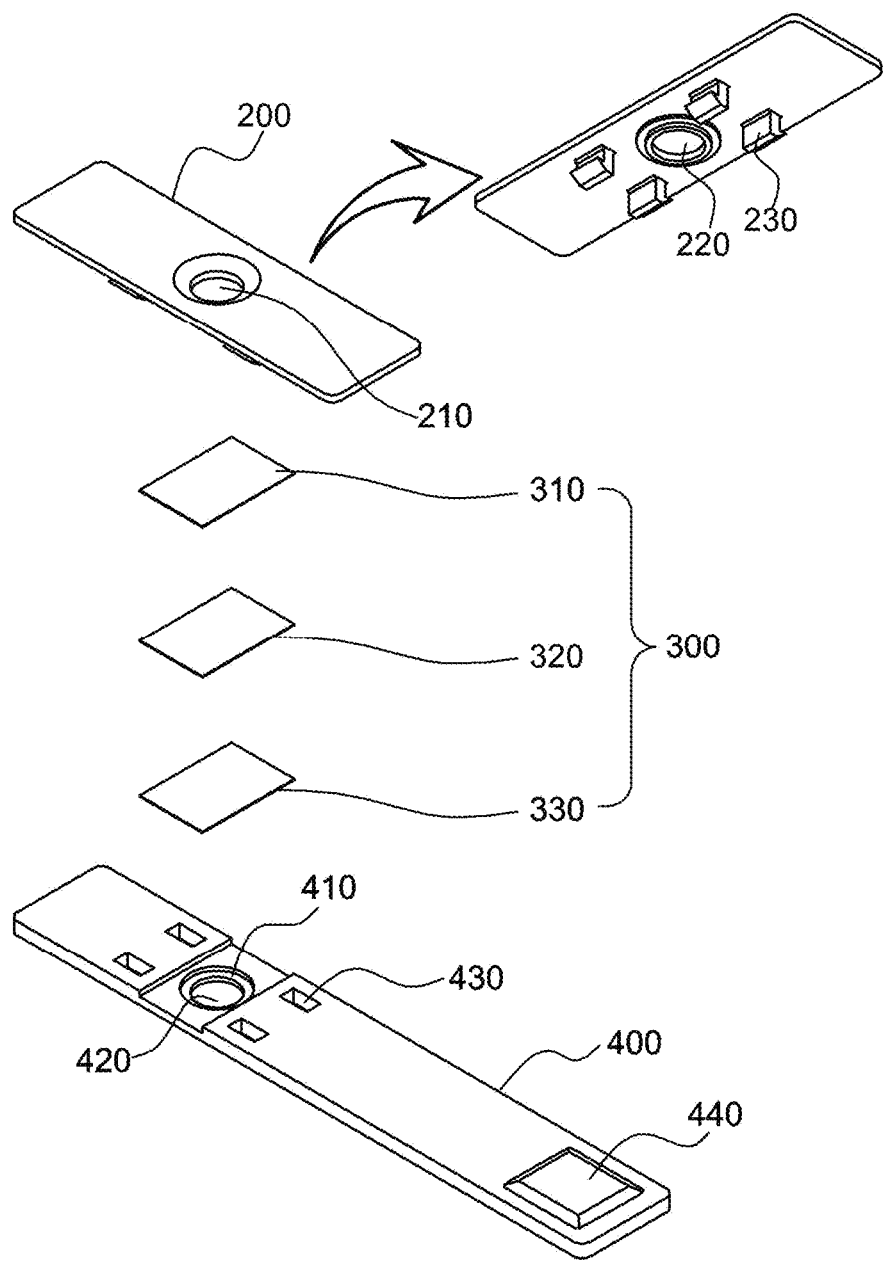
[Figure 1]

[Figure 2]
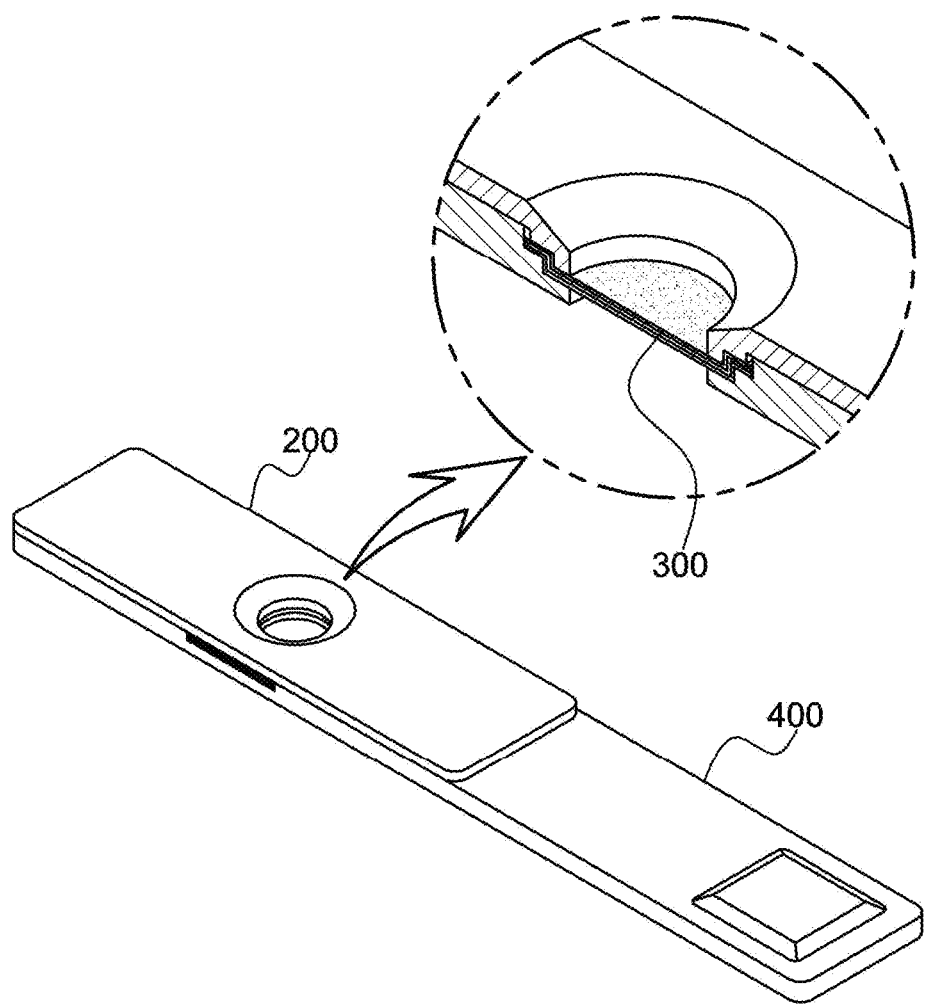

[Figure 3]
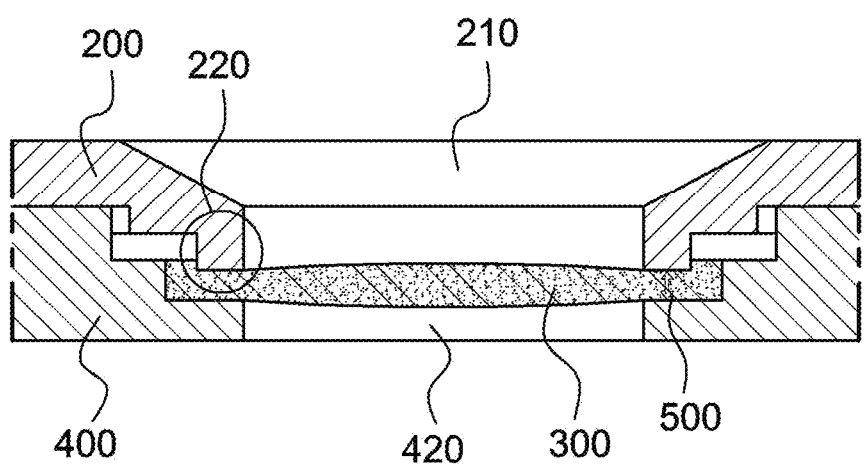

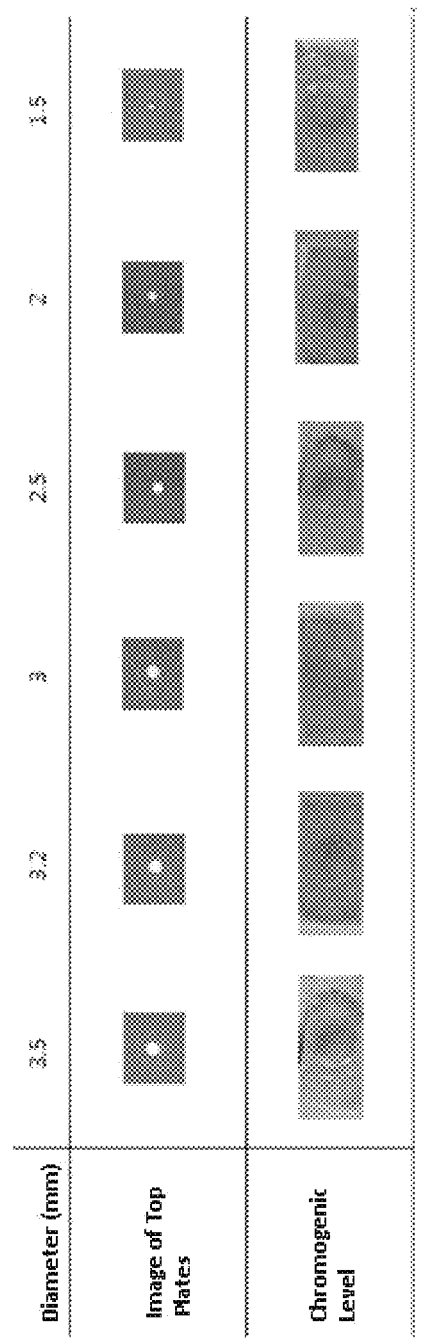
[Figure 4]

[Figure 5]
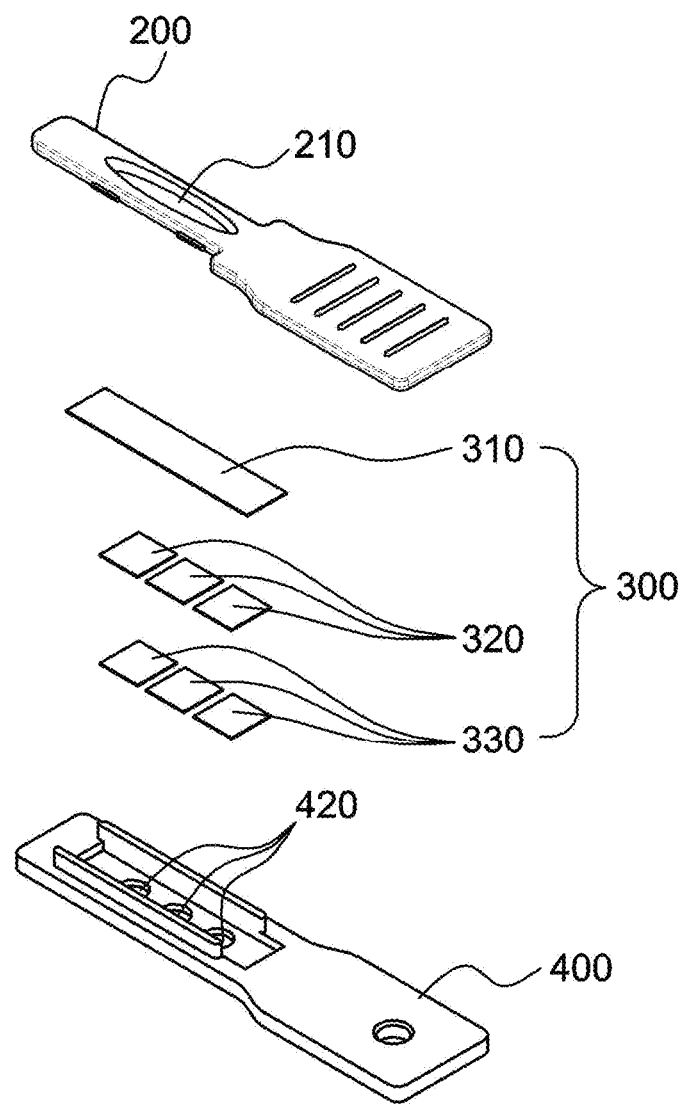

[Figure 6]
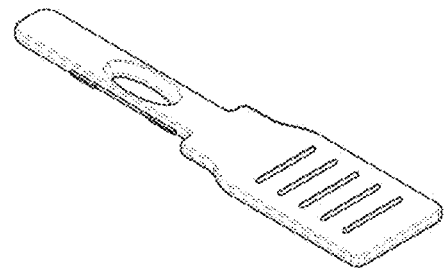
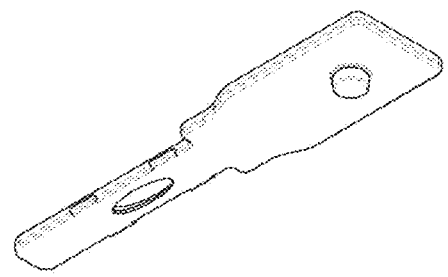
[Figure 7]
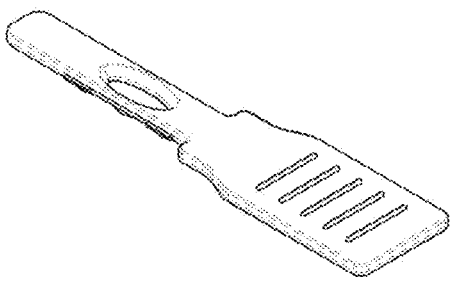
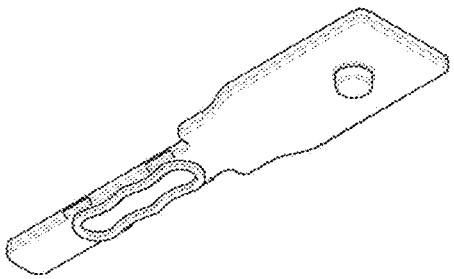

STRIP FOR MEASURING BLOOD LIPIDS

This application is a National Stage of International Application No. PCT/KR2017/014876 filed Dec. 15, 2017, claiming priority based on Korean Patent Application No. 10-2016-0175318 filed Dec. 21, 2016.

TECHNICAL FIELD

The present invention relates to a strip for measuring blood lipids.

BACKGROUND ART

It is chemically or clinically important to quantitatively or qualitatively analyze analytes present in biological samples such as blood. Representative examples include a measurement of cholesterol causing various adult diseases. As technology for measuring biological data such as cholesterol, detections of color changes or electrochemical changes, which are observed when a biological sample such as blood is, for example, dropped on a measuring strip so that an enzymatic reaction occurs in a reaction region, are widely known in the art.

Most strips for measuring a biological sample have a stacked structure in which a plurality of layers containing a reagent are formed between an upper cover and a lower substrate, and also have a vertical structure in which blood moves up and down.

In this regard, Registered Korean Patent No. 10-1058743 entitled "Strip for Measuring Cholesterol and Method of Detecting Cholesterol Using the Same" discloses a strip for measuring biological data and a method of detecting cholesterol using the same, wherein the strip includes an upper cover having at least one blood application part; a red blood cell- and low-density lipoprotein cholesterol-filtering layer disposed below the upper cover to coagulate red blood cells from collected blood and simultaneously perform separation of red blood cells and separation of low-density lipoprotein (LDL) cholesterol while precipitating the low-density lipoprotein cholesterol at the same time; a reaction layer disposed below the red blood cell- and low-density lipoprotein cholesterol-filtering layer and including a cholesterol-measuring reagent which biologically reacts with blood from which the red blood cell- and low-density lipoprotein cholesterol are separated; and a lower support disposed below the reaction layer to support the reaction layer.

For the strip for measuring biological data as described above, it is important to uniformly diffuse blood into the measurement layer when the blood is introduced into the measurement layer. In general, when a biological sample such as blood is added dropwise to a central region of the measurement layer, the blood is spreading from a central region to edges of the measurement layer. In this case, as the blood spreads to the edges of the measurement layer, a flow rate of the blood may be slowed down, and cross-sectional areas of the edges may be slightly different in all directions, resulting in different flow rates in all directions. Therefore, the biological sample may not be evenly or uniformly diffused in all directions from the central region to the edges of the measurement layer. As a result, when the biological sample is not evenly spread to the entire region of the measurement layer, errors may be caused while measuring a quantity of blood lipids using a measuring device. Therefore, it is important to uniformly diffuse the blood to the entire region of the measurement layer. In Registered Korean Patent No. 10-1058743 as described above, there is no proposed solution to the problem. Accordingly, there is an urgent need for research on a method of uniformly diffusing blood to a measurement layer in such a measuring strip to enhance the accuracy of measurement results.

PRIOR-ART DOCUMENTS

Patent Document 1: Registered Korean Patent Publication No. 10-1058743 entitled "Strip for Measuring Cholesterol and Method of Detecting Cholesterol Using the Same"
Patent Document 2: Registered Korean Patent Publication No. 10-1191329 entitled "Test Strip for Analyzing Biomaterials"

DISCLOSURE

Technical Problem

To solve the above problems, this applicant have conducted research to attain accurate measurement results by uniformly diffusing blood to a measurement layer of a strip for measuring blood lipids, and found that, when a contact surface of the measurement layer with a protruding part is pressed with an optimal pressure, a structural change in the strip for measuring blood lipids allows the blood to uniformly diffuse to the entire measurement layer. Therefore, the present invention has been completed based on these ideas.

Therefore, an object of the present invention is to provide a strip for measuring blood lipids capable of uniformly diffusing blood to the measurement layer to enhance the accuracy of measurement results.

Technical Solution

To solve the above problems, according to one aspect of the present invention, there is provided a strip for measuring blood lipids, which includes:

an upper cover coupled to a lower substrate and including an upper opening window configured to expose a measurement region of a measurement layer and a protruding part formed to protrude in a coupling direction to the lower substrate along edges of the upper opening window;

a lower substrate coupled to the upper cover and including a recessed part into which the protruding part is inserted by surrounding an external circumference of the protruding part of the upper cover; and a measurement layer configured to determine a reaction with a biological sample, and disposed on the recessed part of the lower substrate and pressed by the protruding part of the upper cover when the lower substrate is coupled to the upper cover, wherein a spacing interval between a bottom part of the protruding part and the bottom of the recessed part when the lower substrate is coupled to the upper cover in a state in which the measurement layer is not inserted is in a range of 0.5 to 0.8 mm.

According to one exemplary embodiment of the present invention, a contact surface of the measurement layer with the protruding part may be pressed between the protruding part and the recessed part so that the biological sample can be uniformly spread in all directions with respect to the measurement layer.

According to one exemplary embodiment of the present invention, the measurement layer may include a diffusion layer configured to diffuse a biological sample to be introduced, a separation layer configured to filter materials other than lipids from the biological sample diffused through the diffusion layer, and a reaction layer configured to react with blood from which the materials other than the lipids are filtered through the separation layer.

According to one exemplary embodiment of the present invention, the separation layer may include a first separation layer and a second separation layer.

According to one exemplary embodiment of the present invention, the reaction layer may cause an optical change through reaction with the biological sample.

According to one exemplary embodiment of the present invention, the optical change may include any one or more selected from color development, discoloration, or an increase or decrease in fluorescence intensity through the reaction with the biological sample.

According to one exemplary embodiment of the present invention, the separation layer may include one or more selected from the group consisting of paper pads, glass fibers, polyester, nitrocellulose, and polysulfonate, and may contain a reagent to precipitate materials other than the blood lipids.

According to one exemplary embodiment of the present invention, the upper cover and the lower substrate may be fastened to each other by means of a fastening hook so that the upper cover and the lower substrate can be stacked and coupled to each other.

According to one exemplary embodiment of the present invention, all or some of the upper cover or the lower substrate may be painted with different colors, depending on the type of blood lipids to be measured, thereby making it possible to determine the type of blood lipids during the measurement.

According to one exemplary embodiment of the present invention, the strip for measuring blood lipids may further include a fixing layer configured to fix the measurement layer to the recessed part of the lower substrate.

According to one exemplary embodiment of the present invention, the bottom part of the recessed part of the lower substrate may include one or more lower opening windows.

According to one exemplary embodiment of the present invention, the measurement layer may include a diffusion layer configured to diffuse a biological sample to be introduced, a separation layer configured to filter materials other than lipids from the biological sample diffused through the diffusion layer, and a reaction layer configured to react with blood from which the materials other than the lipids are filtered through the separation layer; the one or more separation layers and the one or more reaction layers may be present to correspond to the one or more lower opening windows, respectively; and the diffusion layer may be configured in a singular form to cover both the separation layer and the reaction layer.

According to one exemplary embodiment of the present invention, the blood lipids may include one or more selected from the group consisting of total cholesterol, triglycerides, and high-density lipoprotein cholesterol.

According to one exemplary embodiment of the present invention, the one or more blood lipids may be measured at the same time.

Advantageous Effects

The strip for measuring blood lipids according to the present invention is useful in pressing a contact surface of a measurement layer with a protruding part, the measurement layer being disposed between an upper cover and a lower substrate, with an optimal pressure or to an optimal height, so as to improve the uniform diffusion of a biological sample such as blood, thereby enhancing the accuracy of measurement results of the biological sample.

DESCRIPTION OF DRAWINGS

FIG. 1 is an exploded perspective view of a strip 100 for measuring blood lipids according to one exemplary embodiment of the present invention.

FIG. 2 is a combined perspective view of the strip 100 for measuring blood lipids according to one exemplary embodiment of the present invention.

FIG. 3 is a cross-sectional view of a measurement region in the strip 100 for measuring blood lipids according to one exemplary embodiment of the present invention.

FIG. 4 is a diagram showing that blood filtered through upper opening windows having diameters of 1.5, 2, 2.5, 3, 3.2, and 3.5 mm has the same or similar uniform diffusions, regardless of the diameters of the windows (blood sample inlets).

FIG. 5 is an exploded perspective view of a strip for measuring blood lipids according to another exemplary embodiment of the present invention.

FIG. 6 is a schematic diagram showing that no protruding part is provided on an upper substrate of the strip for measuring blood lipids according to another exemplary embodiment of the present invention.

FIG. 7 is a schematic diagram showing that a protruding part is provided on the upper substrate of the strip for measuring blood lipids according to another exemplary embodiment of the present invention.

BEST MODE

Hereinafter, specific embodiments of the present invention will be described in further detail with reference to the accompanying drawings. However, it should be understood that the present invention may be embodied in various forms, but is not intended to be limiting in this context.

In this specification, the term "measurement region" refers to a region of a measurement layer into which blood is introduced and in which a reaction occurs, and may include an upper opening window and a protruding part provided in an upper cover, and a recessed part and a lower opening window provided in a lower substrate.

In this specification, the term "uniform diffusion" refers to a degree of uniform diffusion and distribution of biological samples, and the like.

The present invention provides a strip 100 for measuring blood lipids, which includes an upper cover 200 coupled to a lower substrate 400 and including an upper opening window 210 configured to expose a measurement region of a measurement layer 300 and a protruding part 220 formed to protrude in a coupling direction to the lower substrate 400 along edges of the upper opening window 210;

a lower substrate 400 coupled to the upper cover 200 and including a recessed part 410 into which the protruding part 220 is inserted by surrounding an external circumference of the protruding part 220 of the upper cover 200; and a measurement layer 300 configured to determine a reaction with a biological sample, and disposed on the recessed part 410 of the lower substrate 400 and pressed by the protruding part 220 of the upper cover 200 when the lower substrate 400 is coupled to the upper cover 200, wherein a spacing interval between a bottom part of the protruding part 220 and the bottom of the recessed part 410 when the lower substrate 400 is coupled to the upper cover 200 in a state in which the measurement layer 300 is not inserted is in a range of 0.5 to 0.8 mm.

The blood lipids may include one or more selected from the group consisting of total cholesterol, triglycerides, and high-density lipoprotein cholesterol.

A contact surface of the measurement layer 300 with the protruding part 220 may be pressed between the protruding part 220 and the recessed part 410 so that the biological sample can be uniformly spread in all directions with respect to the measurement layer 300.

FIG. 1 is an exploded perspective view of a strip 100 for measuring blood lipids according to one exemplary embodiment of the present invention.

FIG. 2 is a combined perspective view of the strip 100 for measuring blood lipids according to one exemplary embodiment of the present invention.

FIG. 3 is a cross-sectional view of a measurement region in the strip 100 for measuring blood lipids according to one exemplary embodiment of the present invention.

Referring to FIG. 1, the strip 100 for measuring blood lipids according to the present invention includes an upper cover 200, a lower substrate 400, and a measurement layer 300.

In the strip 100 for measuring blood lipids according to the present invention, the lower substrate 400 is disposed at the bottom, the measurement layer 300 is disposed on a recessed part 410 of the lower substrate 400, and the upper cover 200 is disposed on the lower substrate 400 so that the lower substrate 400 is coupled to the upper cover 200. As a result, the measurement layer 300 may be disposed between the upper cover 200 and the lower substrate 400.

Referring to the cross-sectional view of the measurement region shown in FIG. 3, when the lower substrate 400 is coupled to the upper cover 200, a protruding part 220 of the upper cover 200 is inserted into the recessed part 410 of the lower substrate 400. In this case, a bottom part of the protruding part 220 does not come into contact with the bottom of the recessed part 410, and a spacing interval 500 between the bottom part of the protruding part 220 and the bottom of the recessed part 410 may, for example, be in a range of approximately 0.5 to 0.8 mm. Therefore, a contact surface of the measurement layer 300, which is disposed between the bottom part of protruding part 220 and the bottom of the recessed part 410, with the protruding part 220 may be pressed with an appropriate pressure. The spacing interval 500 refers to a spacing interval 500 between the bottom part of the protruding part 220 and the bottom of the recessed part 410 when the lower substrate 400 is coupled to the upper cover 200 in a state in which the measurement layer 300 is not inserted.

As the contact surface of the measurement layer 300 with the protruding part 220 is pressed with an appropriate pressure, a biological sample such as blood, or the like, which is added dropwise to a central region of the measurement layer 300, may be evenly spread in all outward directions from the central region to the external edges of the measurement layer 300. The contact surface of the measurement layer 300 with the protruding part 220 may refer to a region of the measurement layer 300 which comes into contact with the bottom of the protruding part 220 of the upper cover.

In a configuration in which the contact surface of the measurement layer 300 with the protruding part 220 is not pressed properly, when the biological sample is added dropwise to the central region of the measurement layer 300, the biological sample may be diffused in a direction from the central region to each of the external edges. In this case, as the biological sample is diffused to the edges of the measurement layer 300, a flow rate of the biological sample may be slowed down, and cross-sectional areas of the edges may be slightly different in all directions, resulting in different flow rates in all directions. Therefore, the biological sample may not be evenly or uniformly diffused in all directions from the central region to the edges of the measurement layer 300. When the biological sample is not evenly diffused to the entire region of the measurement layer 300, errors may be caused while measuring a quantity of blood lipids using a measuring device. Accordingly, after the biological sample is added dropwise to the central region of the measurement layer 300, the biological sample should be uniformly spread to the entire region of the measurement layer 300.

When a cross-sectional area of the measurement layer 300 is reduced under a pressure, a flow rate of the biological sample at a point where the biological sample passes through the cross-sectional area increases according to the formula: $U=Q/A$ ($U$=a flow rate, $Q$=a quantity of flow, and $A$=a cross-sectional area). When the contact surface of the measurement layer 300 with the protruding part 220 is pressed uniformly, the cross-sectional areas of the edges may be reduced equally in all directions, resulting in an increased flow rate of a fluid passing through the edges, and the flow rates are identical in all directions. As a result, when the biological sample is diffused to the edges of the measurement layer 300, a decrease in the flow rate does not occur and the cross-sectional area of each of the edges is maintained constant, thereby making it possible for the biological sample to be evenly diffused to the entire region of the measurement layer 300.

In this case, a degree of pressing of the contact surface of the measurement layer 300 with the protruding part 220 may be a parameter for uniform diffusion of the biological sample. Accordingly, the present inventors have found through various comparative experiments that the optimal pressing strength is applied when the spacing interval between the bottom part of the protruding part 220 and the bottom of the recessed part 410 when the lower substrate 400 is coupled to the upper cover 200 is in a range of approximately 0.5 to 0.8 mm, thereby improving uniform diffusion of the biological sample to remarkably improve the reliability of measurement results of the biological sample. More particularly, the spacing interval is in a range of 0.55 to 0.75 mm, further particularly in a range of 0.6 to 0.7 mm, and most particularly in a range of 0.62 to 0.68 mm.

Hereinafter, a configuration of the strip 100 for measuring blood lipids according to the present invention will be described in detail.

The upper cover 200 is coupled to the lower substrate 400, and includes an upper opening window 210 configured to expose a measurement region of the measurement layer 300, and a protruding part 220 formed to protrude in a coupling direction to the lower substrate 400 along edges of the upper opening window 210. A biological sample such as blood may be introduced by adding the biological sample dropwise to the strip 100 through the upper opening window 210. Also, the protruding part 220 serves as a press part configured to press the measurement layer 300, and a shape of the protruding part 220 may be generally determined based on the shape of the upper opening window 210. In this case, the protruding part 220 may be in a polygonal, circular, or amorphous shape, and particularly in a circular shape.

A width (i.e. a diameter when it is in a circular shape) of the upper opening window 210 is proportional to a distance between the protruding part 220 and the central region of the upper opening window 210 to which pressure is applied. In this case, it was confirmed that such a width of the upper opening window 210 does not have an influence on the uniform diffusion of the biological sample when it is in a range of 1.5 to 10 mm. Therefore, the width of the upper opening window 210 may be in a range of 1.5 to 10 mm, more particularly in a range of 1.5 to 7 mm, further particularly in a range of 1.5 to 5 mm, and most particularly in a range of 1.5 to 3.5 mm.

Referring again to the bottom view of the upper cover 200 shown in FIG. 1, the upper cover 200 may have a male hook 230 in a coupling direction to the lower substrate 400 for strong coupling and fastening to the lower substrate 400.

The lower substrate 400 is coupled to the upper cover 200, and includes a recessed part 410 into which the protruding part 220 is inserted by surrounding an external circumference of the protruding part 220 of the upper cover 200. The measurement layer 300 may be disposed and fixed in the recessed part 410. When the lower substrate 400 is coupled to the upper cover 200 after the disposition of the measurement layer 300, the protruding part 220 of the upper cover 200 is inserted into the recessed part 410, thereby pressing the contact surface of the measurement layer 300, which is disposed on the recessed part 410, with the protruding part 220. The bottom part, that is, the bottom of the recessed part 410 may be in a flat shape, but the present invention is not limited thereto. Referring to the cross-sectional view shown in FIG. 3, according to one exemplary embodiment of the present invention, because a second recessed part (not shown) may be further formed in the recessed part 410, the cross section of the second recessed part may be formed in a stepped fashion. That is, one cross section of the recessed part 410 may be in a 'L' shape.

The protruding part 220 may also be in a '⊓' shape in which a gradually narrowing second protruding part (not shown) is additionally formed to correspond to the formation of such a second recessed part. In this case, a stepped coupling section may be formed by inserting the protruding part 220 into the recessed part 410 and simultaneously inserting the second protruding part into the second recessed part. In this case, the spacing interval may be a distance between the bottom part of the second protruding part and the bottom of the second recessed part.

The bottom part of the recessed part 410 of the lower substrate 400 may include a lower opening window 420. Because the upper opening window 210 of the upper cover 200 is disposed linearly with respect to the lower opening window 420 of the lower substrate 400 when the lower substrate 400 is coupled to the upper cover 200, upper and lower surfaces of the measurement region, which is in the same position as the measurement layer 300 disposed therebetween, may be opened and exposed to upper and lower sides of the strip 100.

Also, the lower substrate 400 may have a female hook 430 for strong fastening to the upper cover 200.

When the upper cover 200 is stacked on the lower substrate 400 and assembled in a state in which the measurement layer 300 is disposed on the recessed part 410 of the lower substrate 400, a region of the lower substrate 400 which is not covered with the upper cover 200, that is, one lateral end of the lower substrate 400 may be a gripping part 440 which a user holds with one hand.

The strip 100 for measuring blood lipids may further include a fixing layer (not shown) configured to fix the measurement layer 300 to the inside of the recessed part 410 of the lower substrate 400. When the measurement layer 300 is allowed to move slightly in the recessed part 410 of the lower substrate 400, it may have an influence on the measurement results. As a result, it is necessary to stably fix the measurement layer 300 to the recessed part 410 of the lower substrate 400. Therefore, a fixing layer such as 3M double-sided adhesive tape may, for example, be introduced between the bottom part of the recessed part 410 and the measurement layer 300 to prevent movement of the measurement layer 300.

In this case, the spacing interval 500 between the bottom part of the protruding part 220 of the upper cover 200 and the bottom of the recessed part 410 of the lower substrate 400 may be replaced with a distance between the bottom part of the protruding part 220 and the fixing layer. In this case, because the spacing interval 500 may be maintained in a constant distance of 0.5 to 0.8 mm, the measurement layer 300 may be pressed with the same pressure.

Also, all or some of the upper cover 200 or the lower substrate 400 may be painted with different colors, depending on the type of blood lipids to be measured, thereby making it possible to determine the type of blood lipids during the measurement. For example, the upper cover 200 or the lower substrate 400 may be painted red to measure the total cholesterol, the upper cover 200 or the lower substrate 400 may be painted yellow to measure the triglycerides, or the upper cover 200 or the lower substrate 400 may be painted blue to measure the high-density lipoprotein cholesterol, but the present invention is not limited thereto. In this case, it is convenient because the type of the blood lipids may be directly determined based on the color of the upper cover 200 or the lower substrate 400 during the measurement of the blood lipids.

Referring to FIG. 2, the upper cover 200 and the lower substrate 400 may be fastened to each other by means of a fastening hook so that the upper cover 200 and the lower substrate 400 can be stacked and coupled to each other. When the lower substrate 400 is coupled to the upper cover 200 by means of the fastening hook, an increase in fastening strength may allow the protruding part 220 to stably and uniformly press the contact surface of the measurement layer 300 with the protruding part 220 while measuring the blood lipids using a measuring device, resulting in improved measurement accuracy.

The measurement layer 300 may include a diffusion layer 310 configured to diffuse a biological sample to be introduced, a separation layer 320 configured to filter materials other than lipids from the biological sample diffused through the diffusion layer 310, and a reaction layer 330 configured to react with blood from which the materials other than the lipids are filtered through the separation layer 320.

As shown in FIG. 1, the measurement layer 300 according to one exemplary embodiment of the present invention may be realized in a shape in which the diffusion layer 310, the separation layer 320, and the reaction layer 330 are stacked. In general, a thickness of the measurement layer 300 prior to the pressing process may be in a range of 0.85 to 0.95 mm The diffusion layer 310 serves to rapidly and uniformly diffuse a biological sample to be introduced, such as blood, and the like. According to one exemplary embodiment of the present invention, the diffusion layer 310 may, for example, be a woven material such as polyester or cotton or a non-woven fabric such as fabrics, gauze, monofilaments.

The separation layer 320 is provided below the diffusion layer 310, and may serve to filter materials other than lipids from a biological sample, that is, blood diffused through the diffusion layer 310. The materials other than the lipids may include blood cells such as red blood cells, and the like.

According to one exemplary embodiment of the present invention, the separation layer 320 may experimentally filter approximately 80 to 90% of the total red blood cells. Also, the separation layer 320 may include a first separation layer and a second separation layer. In this case, blood cells may be filtered through the second separation layer when the blood cells are not filtered through the first separation layer.

The separation layer 320 may include one or more selected from the group consisting of paper pads, glass fibers, polyester, nitrocellulose, and polysulfonate. According to one exemplary embodiment of the present invention, the separation layer 320 may include a reagent to precipitate the materials other than the blood lipids to be measured. When the biological sample is introduced into the measurement layer 300, the blood from which the remaining materials other than one of blood lipids to be measured in the biological sample, for example, total cholesterol, triglycerides, or high-density lipoprotein cholesterol are filtered through the separation layer 320 may be introduced into the reaction layer 330. In this case, the separation layer 320 may have a caliber of .5to 2 μm and a thickness of 0.10 to 0.40 mm, more particularly 0.20 to 0.40 mm, and most particularly 0.30 to 0.35 mm.

The reagent may include a coagulant, a precipitating agent, or a mixture thereof, may be evenly distributed over the entire separation layer 320, and may present in an impregnated or fixed form. For example, when the reagent is intended to measure total cholesterol and triglycerides, the coagulant may be composed of lectin, a cationic polymer, or a saccharide. For example, the lectin includes phytohemagglutinin (PHA), concanavalin A, pokeweed mitogens (PWMs), and agglutinin in malt, but the present invention is not limited thereto. For example, the cationic polymer may include poly(diallyldimethylammonium chloride), and the saccharide may include one or more selected from a monosaccharide, a disaccharide, or a polysaccharide. For measurement of the high-density lipoprotein cholesterol, the coagulant may be composed of lectin, a cationic polymer, or a saccharide. For example, the lectin includes phytohemagglutinin (PHA), concanavalin A, pokeweed mitogens (PWMs), and agglutinin in malt, but the present invention is not limited thereto. For example, the cationic polymer may include poly(diallyldimethylammonium chloride), and the saccharide may include one or more selected from a monosaccharide, a disaccharide, or a polysaccharide, for example, sorbitol, sugar, or oligosaccharides, but the present invention is not limited thereto. The precipitating agent serves to selectively precipitate the low-density lipoprotein (LDL) cholesterol in blood depending on the concentration of the precipitating agent, and includes one of a sulfonated polysaccharide, heparin, phosphotungstic acid (PTA), and dextran sulfate, one of which may include group 2 cations.

The reaction layer 330 is provided below the separation layer 320, and may include a reagent that causes a reaction with a biological sample from which the materials other than blood cells and lipids to be measured are filtered through the separation layer 320, that is, a color change.

The reaction layer 330 may react with the blood from which the materials other than the lipids to be measured are filtered through the separation layer 320 so as to obtain the biological data. The reaction layer 330 includes a reagent that may cause a reaction with the lipids to be measured, and such a reagent is present in a state in which the reagent is impregnated or fixed in the reaction layer 330.

For example, when the high-density lipoprotein cholesterol is measured according to one exemplary embodiment of the present invention, an optical change is observed by allowing cholesterol to react with a cholesterol esterase so that the cholesterol is degraded into free cholesterol and fatty acids, followed by allowing a peroxidase and a chromogenic reagent to react with a cholesterol oxidase, the free cholesterol, and hydrogen peroxide generated by an aerobic reaction. Accordingly, the high-density lipoprotein cholesterol may be quantified based on these results.

When the total cholesterol is measured according to one exemplary embodiment of the present invention, an optical change is observed by allowing a peroxidase and chromogenic reagent to react with free cholesterol generated by a reaction of cholesterol ester with an esterase, a cholesterol oxidase, and hydrogen peroxide generated by a reaction with oxygen. Accordingly, the total cholesterol may be quantified based on these results.

When the triglyceride is measured according to one exemplary embodiment of the present invention, an optical change is observed by allowing peroxidase and a chromogenic reagent to react with a product phosphorylated by allowing glycerol generated by a reaction of triglycerides with a lipase to react with a glycerol kinase in the presence of ATP, an oxidase, and a hydrogen peroxide solution generated by a reaction with oxygen. Accordingly, the triglyceride may be quantified based on these results.

According to exemplary embodiments of the present invention, a configuration of the measurement layer 300 may include various modifications, but the present invention is not limited thereto. For example, additional layers may be further included between the respective layers so as to further improve an absorption rate of the biological sample or a mutual transfer rate of the biological sample between the respective layers. Specifically, additional diffusion layers 310 may be inserted between the respective layers to facilitate the more rapid diffusion.

Also, as shown in FIG. 5, one upper opening window 210, one diffusion layer 310, a plurality of separation layers 320, a plurality of reaction layers 330, and a plurality of lower opening windows 420 are provided. Therefore, it is possible to add a biological sample dropwise through the one upper opening window 210 to observe the reaction to a plurality of detection materials through the separate lower opening windows 420.

In this case, the separation layer 320 and the reaction layer 330 correspond to the respective lower opening windows 420, and the diffusion layer is configured in a singular form to cover both the plurality of separation layers 320 and reaction layers 330. As a result, the plurality of measurement regions may be formed. Also, the upper opening window 210 may be formed with a suitable size to cover both the plurality of separation layers 320 and reaction layers 330.

From these results, the strip 100 for measuring blood lipids according to the present invention may measure information of various biological samples at the same time. As shown in FIG. 5 of the present invention, a plurality (3) of measurement regions are formed in one strip 100 for measuring blood lipids, thereby making it possible to measure one or more blood lipids at the same time. Specifically, the blood lipids may include one or more selected from the group consisting of total cholesterol, triglycerides, and high-density lipoprotein cholesterol. For example, the separation layer 320 and the reaction layer 330 in the measurement layer 300 shown in FIG. 5 may be formed to measure the total cholesterol, to measure the triglycerides, and to measure the high-density lipoprotein cholesterol, respectively.

MODE FOR INVENTION

Hereinafter, preferred embodiments of the present invention are provided to aid in understanding the present invention. However, it should be appreciated by those skilled in the art that the detailed description disclosed herein is given by way of illustration of the present invention only, and thus various changes and modifications may be made without departing from the sprite and scope of the present invention. Also, it will be apparent that such changes and modifications fall within the appended claims.

Example and Comparative Examples

1. Confirmation of Effect of Diameter of Upper Opening Window of Single-Opening Strip on Blood Diffusion Upper opening windows were formed to have diameters of 1.5, 2, 2.5, 3, 3.2, and 3.5 mm, and subjected to experiments. Referring to FIG. 4, blood which had passed through the upper opening windows was immediately spread to the measurement layer, and the uniform spreading of the blood was observed regardless of the diameters of the upper opening windows (blood inlets). In this case, the single-opening strip may refer to a strip in the form as shown in FIG. 1, which is able to measure each of the total cholesterol, the triglycerides, and the high-density lipoprotein cholesterol in a single round.

2. Estimation of Optimal Spacing Interval of Single-Opening Strip

To determine the uniform diffusion of the biological sample to the measurement layer according to the spacing interval between the bottom part of the protruding part of the upper cover and the bottom of the recessed part of the lower substrate in the strip for measuring blood lipids according to the present invention, the lipids to be measured were selected from total cholesterol, triglycerides, or high-density lipoprotein cholesterol, and the spacing interval was set to 0.65 mm (Example 1), 0.45 mm (Comparative Example 1), or 0.85 mm (Comparative Example 2) to manufacture a strip for measuring blood lipids. A blood sample was introduced dropwise through the opening window of the upper cover of each of the strips for measuring blood lipids manufactured in Example 1 and Comparative Examples 1 and 2, and a flow pattern of the blood was then observed. Then, the results of the total cholesterol, the triglycerides, or the high-density lipoprotein cholesterol are listed in Table 1 below.

TABLE 1

| Spacing interval (mm) | Total cholesterol (Cv %) | Triglyceride (Cv %) | High-density lipoprotein cholesterol (Cv %) |
|---|---|---|---|
| 0.45 (Comparative Example 1) | 5% | 5% | 7% |
| 0.65 (Example 1) | 3% | 3% | 4% |
| 0.85 (Comparative Example 2) | 5% | 4% | 7% |

The CV % refers to a coefficient of variation, and means that the size of standard deviation is expressed by a percentage of the mean. In this case, the CV % may be used as an indicator of reproducibility, and the lower CV % means the higher reproducibility of measurements.

As listed in Table 1 above, when the spacing interval between the bottom part of the protruding part of the upper cover and the bottom of the recessed part of the lower substrate in the strip for measuring blood lipids was 0.65 mm, as shown in Example 1, the CV % value was 3% in the case of the total cholesterol and the triglycerides, and 4% in the case of the high-density lipoprotein cholesterol. Therefore, it can be seen that the strip for measuring blood lipids showed superior reproducibility, compared to those of Comparative Examples 1 and 2, and had excellent resolution because the strip had the highest grade value as an indicator of resolution.

3. Estimation of Optimal Spacing Interval of 3-Opening Strip

The strip for measuring blood lipids according to one exemplary embodiment of the present invention may measure the total cholesterol, the triglycerides, and the high-density lipoprotein cholesterol separately or simultaneously. When the blood lipids were able to be measured separately, a single-opening strip may be realized to consist of the upper cover 200 and the lower substrate 400 as in the configuration of FIG. 1. Also, when the plurality of blood lipids are measured simultaneously, the strip may be realized to consist of the upper cover 200 and the lower substrate 400 as in the configuration of FIG. 5. In this case, the strip may be obtained as a 3-opening strip having a structure in which the upper cover has one open window 210 and the lower substrate has 3 open windows 420.

Also, to determine the uniform diffusion of the biological sample to the measurement layer according to the spacing interval between the bottom part of the protruding part of the upper cover and the bottom of the lower substrate, the upper cover having no protruding part was designed as shown in FIG. 6, and the upper cover having a protruding part was designed as shown in FIG. 7. Thereafter, both the upper covers were subjected to comparative experiments.

A blood sample was introduced dropwise through the opening window of the upper cover of the strips for measuring blood lipids, and a flow pattern of the blood was then observed. Then, the results of simultaneous measurement of the total cholesterol, the triglycerides, or the high-density lipoprotein cholesterol are listed in Table 2 below.

TABLE 2

| Spacing interval (mm) | Total cholesterol (CV %) | Triglyceride (CV %) | High-density lipoprotein cholesterol (CV %) |
|---|---|---|---|
| Non-protruding part | 5% | 5% | 7% |
| Protruding part | Less than 3% | Less than 3% | Less than 4% |

The CV % refers to a coefficient of variation, and means that the size of standard deviation is expressed by a percentage of the mean. In this case, the CV % may be used as an indicator of reproducibility, and the lower CV % means the higher reproducibility of measurements.

As listed in Table 2 above, when the protruding part is present between the upper cover and the bottom of the recessed part of the lower substrate in the strip for measuring blood lipids, as described in the single-opening strip, the CV % values were less than 3%, less than 3%, and less than 4% in the case of the total cholesterol, the triglycerides, and the high-density lipoprotein cholesterol, respectively. Therefore, it was confirmed that the strip for measuring blood lipids had superior reproducibility, compared to when the upper cover had a non-protruding part.

BRIEF DESCRIPTION OF MAIN PARTS IN THE DRAWINGS

100: strip for measuring blood lipids    200: upper cover
210: upper opening window    220: protruding part

| | |
|---|---|
| 230: male hook | 300: measurement layer |
| 310: diffusion layer | 320: separation layer |
| 330: reaction layer | 400: lower substrate |
| 410: recessed part | 420: lower opening window |
| 430: female hook | 440: gripping part |
| 500: spacing interval | |

The invention claimed is:

1. A strip for measuring blood lipids comprising:
an upper cover comprising an upper opening window and a protruding part formed along edges of the upper opening window;
a lower substrate coupled to the upper cover and comprising a recessed part to receive the protruding part of the upper cover by surrounding an external circumference of the protruding part of the upper cover; and
a measurement layer aligned over the recessed part of the lower substrate and exposed through the upper opening window for observation and comprising a compressed portion and a non-compressed portion, wherein the compressed portion is compressed between the recessed part of the lower substrate and the protruding part of the upper cover, and wherein the non-compressed portion has a thickness of 0.85 mm to 0.95 mm and the compression portion has a thickness in a range of 0.5 to 0.8 mm; and
wherein the measurement layer compressed between the recessed part of the lower substrate and the protruding part of the upper cover uniformly spreads a biological sample supplied to the measurement layer in all directions with regard to the measurement layer.

2. The strip for measuring blood lipids according to claim 1, wherein the measurement layer comprises a diffusion layer configured to diffuse a biological sample to be introduced, a separation layer configured to filter materials other than lipids from the biological sample diffused through the diffusion layer, and a reaction layer configured to react with blood from which the materials other than the lipids are filtered through the separation layer.

3. The strip for measuring blood lipids according to claim 2, wherein the reaction layer comprises a reagent that reacts with lipids in the biological sample, said reaction results in an optical change.

4. The strip for measuring blood lipids according to claim 3, wherein the optical change comprises any one or more selected from color development, discoloration, or an increase or decrease in fluorescence intensity through the reaction with the biological sample.

5. The strip for measuring blood lipids according to claim 2, wherein the separation layer comprises one or more selected from the group consisting of paper pads, glass fibers, polyester, nitrocellulose, and polysulfonate, and contains a reagent to precipitate materials other than the blood lipids.

6. The strip for measuring blood lipids according to claim 1, wherein the upper cover and the lower substrate are fastened to each other by means of a fastening hook so that the upper cover and the lower substrate are stacked and coupled to each other.

7. The strip for measuring blood lipids according to claim 1, wherein all or some of the upper cover or the lower substrate is painted with different colors, depending on the type of blood lipids to be measured, thereby making it possible to determine the type of blood lipids during the measurement.

8. The strip for measuring blood lipids according to claim 1, wherein the strip for measuring blood lipids further comprises a fixing layer configured to fix the measurement layer to the recessed part of the lower substrate.

9. The strip for measuring blood lipids according to claim 1, wherein the bottom part of the recessed part of the lower substrate comprises one or more lower opening windows.

10. The strip for measuring blood lipids according to claim 9, wherein the measurement layer comprises a diffusion layer configured to diffuse a biological sample to be introduced, a separation layer configured to filter materials other than lipids from the biological sample diffused through the diffusion layer, and a reaction layer configured to react with blood from which the materials other than the lipids are filtered through the separation layer;
the separation layer and the reaction layer are stacked and aligned to each of the one or more lower opening windows; and
the diffusion layer is configured in a singular form to cover both the separation layer and the reaction layer.

11. The strip for measuring blood lipids according to claim 9, wherein one or more blood lipids are measured at the same time.

12. The strip for measuring blood lipids according to claim 11, wherein the one or more blood lipids comprise one or more selected from the group consisting of total cholesterol, triglycerides, and high-density lipoprotein cholesterol.

13. The strip for measuring blood lipids according to claim 10, wherein one or more blood lipids are measured at the same time.

14. The strip for measuring blood lipids according to claim 13, wherein the one or more blood lipids comprise one or more selected from the group consisting of total cholesterol, triglycerides, and high-density lipoprotein cholesterol.

* * * * *